US012303281B2

(12) United States Patent
Govari et al.

(10) Patent No.: US 12,303,281 B2
(45) Date of Patent: May 20, 2025

(54) MAPPING RESOLUTION OF ELECTROPHYSIOLOGICAL (EP) WAVE PROPAGATING ON THE SURFACE OF PATIENT HEART

(71) Applicant: BIOSENSE WEBSTER (ISRAEL) LTD., Yokneam (IL)

(72) Inventors: Assaf Govari, Haifa (IL); Andres Claudio Altmann, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 861 days.

(21) Appl. No.: 17/354,513

(22) Filed: Jun. 22, 2021

(65) Prior Publication Data

US 2022/0000411 A1    Jan. 6, 2022

Related U.S. Application Data

(63) Continuation-in-part of application No. 16/918,972, filed on Jul. 1, 2020, now Pat. No. 11,730,413.

(51) Int. Cl.
*A61B 5/367* (2021.01)
*A61B 5/287* (2021.01)
*A61B 5/341* (2021.01)

(52) U.S. Cl.
CPC .............. *A61B 5/367* (2021.01); *A61B 5/287* (2021.01); *A61B 5/341* (2021.01)

(58) Field of Classification Search
None
See application file for complete search history.

(56) References Cited

U.S. PATENT DOCUMENTS

| 6,226,542 | B1 | 5/2001 | Reisfeld |
| 6,236,883 | B1 | 5/2001 | Ciaccio et al. |
| 6,301,496 | B1 | 10/2001 | Reisfeld |
| 6,892,091 | B1 | 5/2005 | Ben-Haim et al. |

(Continued)

FOREIGN PATENT DOCUMENTS

| CN | 108348155 B | 2/2019 |
| CN | 110179458 A | 8/2019 |

(Continued)

OTHER PUBLICATIONS

Extended European Search Report dated Nov. 9, 2022 from corresponding EP Application 22180070.9-1113.

(Continued)

*Primary Examiner* — Carl H Layno
*Assistant Examiner* — Manolis Pahakis

(57) ABSTRACT

A system includes a processor to receive multiple electrophysiological (EP) signals acquired by multiple electrodes of a multi-electrode catheter that are in contact with tissue in a region of a cardiac chamber, and respective tissue locations at which the electrodes acquired the EP signals. The processor calculates local activation time (LAT) values for the respective tissue locations, and compares the average LAT values to determine representative locations. Based on a comparison between average LAT values the processor produces a propagation vector indicative of a propagation of an EP wave that has generated the EP signals and displays the propagation vector to a user.

11 Claims, 5 Drawing Sheets

(56) References Cited

U.S. PATENT DOCUMENTS

| | | |
|---|---|---|
| 7,536,218 B2 | 5/2009 | Govari et al. |
| 7,736,218 B2 | 6/2010 | Mayerle et al. |
| 7,756,576 B2 | 7/2010 | Levin |
| 8,456,182 B2 | 6/2013 | Bar-Tal et al. |
| 9,050,011 B2 | 6/2015 | Rubinstein et al. |
| 10,842,572 B1 | 11/2020 | Viswanathan |
| 11,439,339 B1* | 9/2022 | Lux ................ A61B 5/346 |
| 2003/0023130 A1 | 1/2003 | Ciaccio et al. |
| 2004/0243012 A1 | 12/2004 | Ciaccio et al. |
| 2013/0079650 A1* | 3/2013 | Turgeman ........... A61B 5/743 600/509 |
| 2013/0245473 A1* | 9/2013 | Ramanathan ........ A61B 5/318 600/509 |
| 2013/0324871 A1 | 12/2013 | Dubois et al. |
| 2014/0176531 A1* | 6/2014 | Rubinstein ............ G06T 19/00 345/419 |
| 2014/0336518 A1* | 11/2014 | Shuros ................ A61B 5/6858 600/509 |
| 2016/0045123 A1* | 2/2016 | Bar-Tal ................ A61B 5/287 600/515 |
| 2016/0089048 A1 | 3/2016 | Brodnick et al. |
| 2016/0106376 A1* | 4/2016 | Li ........................ A61B 5/349 600/373 |
| 2017/0014086 A1* | 1/2017 | Li ........................ A61B 5/6852 |
| 2017/0042449 A1 | 2/2017 | Deno et al. |
| 2017/0049348 A1 | 2/2017 | Deno et al. |
| 2017/0055864 A1* | 3/2017 | Han ..................... A61B 5/316 |
| 2017/0202471 A1 | 7/2017 | Urman et al. |
| 2017/0202515 A1* | 7/2017 | Zrihem ............... A61B 5/6858 |
| 2017/0246461 A1 | 8/2017 | Ghosh |
| 2017/0281031 A1* | 10/2017 | Houben ............. A61B 18/1492 |
| 2017/0311833 A1 | 11/2017 | Afonso et al. |
| 2017/0332971 A1 | 11/2017 | Macneil et al. |
| 2018/0153426 A1 | 6/2018 | Thakur et al. |
| 2019/0069792 A1* | 3/2019 | Shariat .................. A61B 5/316 |
| 2019/0076045 A1 | 3/2019 | Katz et al. |
| 2019/0259490 A1* | 8/2019 | Cohen ................... A61B 5/339 |
| 2019/0328258 A1* | 10/2019 | Gaeta .................... A61B 5/282 |
| 2020/0060568 A1 | 2/2020 | Katz et al. |
| 2020/0113465 A1 | 4/2020 | Cohen et al. |
| 2020/0146579 A1* | 5/2020 | Bar-Tal ................. A61B 5/349 |
| 2021/0127999 A1* | 5/2021 | Govari .................. A61B 5/743 |
| 2021/0128006 A1* | 5/2021 | Richer .................. A61B 5/364 |
| 2021/0133516 A1* | 5/2021 | Govari .................. A61B 5/743 |
| 2021/0169421 A1 | 6/2021 | Govari |
| 2021/0282659 A1* | 9/2021 | Govari .................. A61B 5/367 |
| 2021/0361215 A1* | 11/2021 | Deno .................... A61B 5/341 |

FOREIGN PATENT DOCUMENTS

| | | |
|---|---|---|
| CN | 111035382 A | 4/2020 |
| CN | 112639990 A | 4/2021 |
| EP | 3639740 A1 | 4/2020 |
| EP | 3649930 A1 | 5/2020 |
| JP | 2017514536 A | 6/2017 |
| JP | 2018526107 A | 9/2018 |
| JP | 2019177135 A | 10/2019 |
| JP | 2020062403 A | 4/2020 |
| JP | 2021512694 A | 5/2021 |
| WO | 2019156755 A1 | 8/2019 |

OTHER PUBLICATIONS

Extended European Search Report dated Nov. 3, 2021, from corresponding EP Application No. 21182626.8.

U.S. Appl. No. 16/708,285, filed Dec. 9, 2019.

Search Report with English translation dated Feb. 12, 2025, from corresponding Japanese Application No. 2021-108540.

Notice of Reasons for Refusal with English translation dated Feb. 18, 2025, from corresponding Japanese Application No. 2021-108540.

* cited by examiner

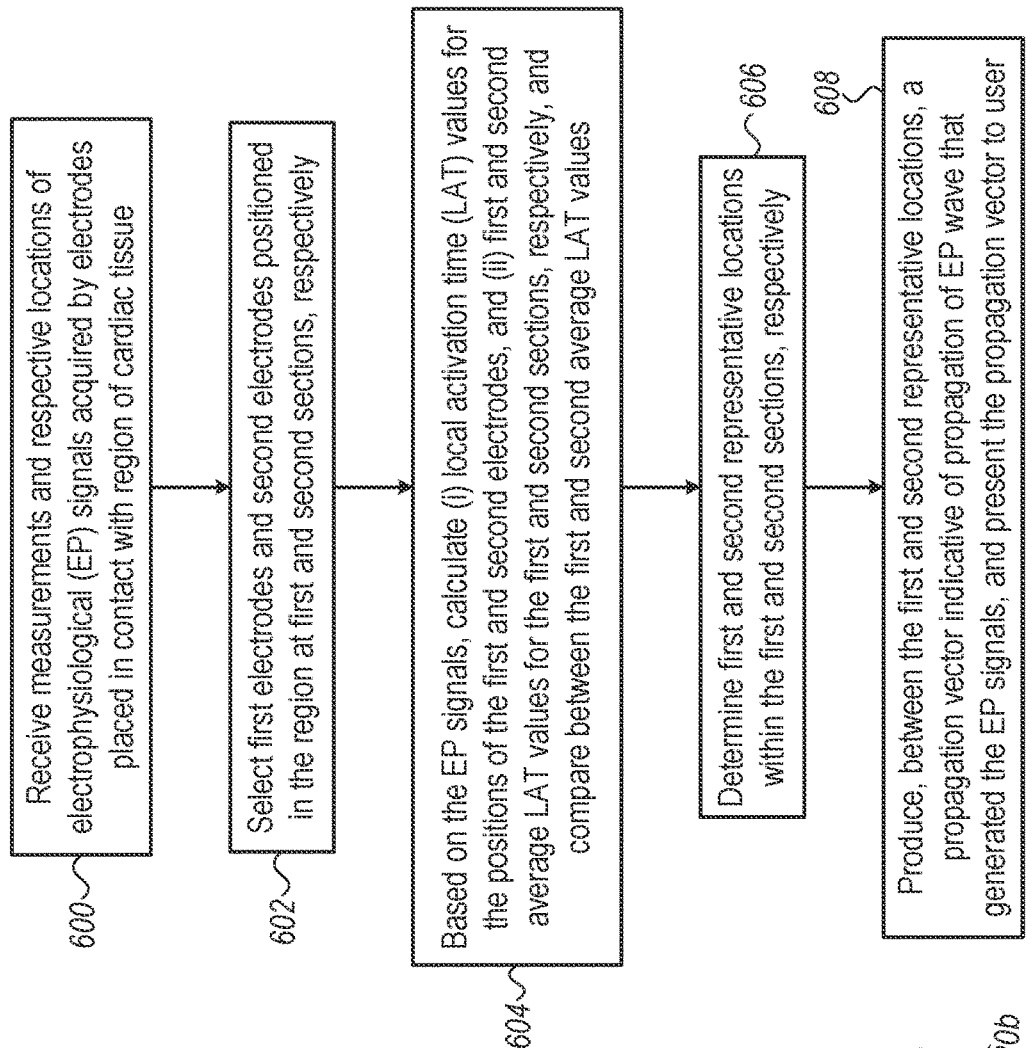
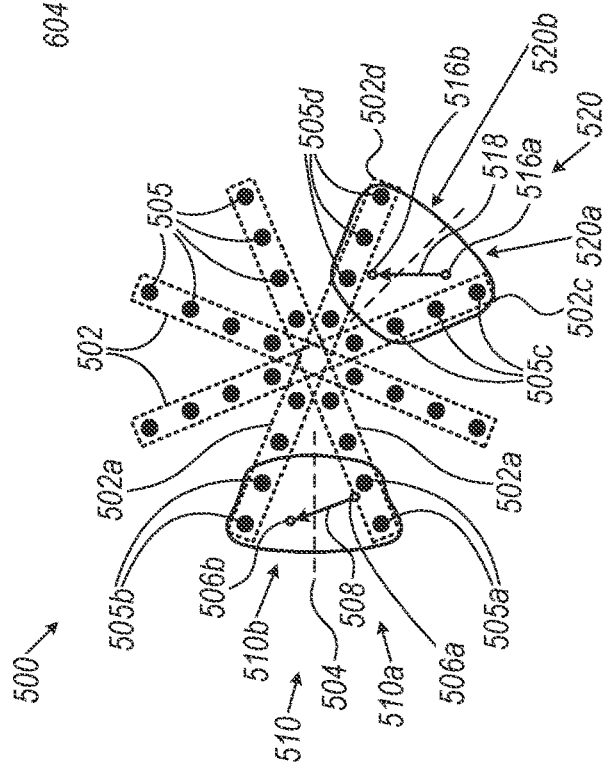

MAPPING RESOLUTION OF ELECTROPHYSIOLOGICAL (EP) WAVE PROPAGATING ON THE SURFACE OF PATIENT HEART

CROSS-REFERENCE TO RELATED APPLICATIONS

This application is a continuation-in-part of U.S. patent application Ser. No. 16/918,972, filed Jul. 1, 2020, now U.S. Pat. No. 11,730,413, whose disclosure is incorporated herein by reference.

FIELD OF THE INVENTION

The present invention relates generally to electrophysiological mapping, and particularly to cardiac electrophysiological mapping.

BACKGROUND OF THE INVENTION

Invasive cardiac techniques for mapping electrophysiological (EP) properties of cardiac tissue were previously proposed in the patent literature. For example, U.S. Patent Application Publication 2017/0311833 describes an efficient system for diagnosing arrhythmias and directing catheter therapies that may allow for measuring, classifying, analyzing, and mapping spatial EP patterns within a body. The efficient system may further guide arrhythmia therapy and update maps as treatment is delivered. The efficient system may use a medical device having a high density of sensors with a known spatial configuration for collecting EP data and positioning data. Further, the efficient system may also use an electronic control system for computing and providing the user with a variety of metrics, derivative metrics, high definition (HD) maps, HD composite maps, and general visual aids for association with a geometrical anatomical model shown on a display device.

As another example, U.S. Patent Application Publication 2017/0042449 describes a system for determining EP data, the system comprising an electronic control unit configured to acquire electrophysiology signals from a plurality of electrodes of one or more catheters, select at least one clique of electrodes from the plurality of electrodes to determine a plurality of local E field data points, determine the location and orientation of the plurality of electrodes, process the electrophysiology signals from the at least one clique from a full set of bi-pole sub-cliques to derive the local E field data points associated with the at least one clique of electrodes, derive at least one orientation independent signal from the at least one clique of electrodes from the information content corresponding to weighted parts of electrogram signals, and display or output catheter-orientation-independent EP information to a user or process.

U.S. Patent Application Publication 2018/0153426 describes method and system for mapping an anatomical structure, that include sensing activation signals of intrinsic physiological activity with a plurality of mapping electrodes disposed in or near the anatomical structure, each of the plurality of mapping electrodes having an electrode location. A vector field map which represents a direction of propagation of the activation signals at each electrode location is generated to identify a signature pattern and a location in the vector field map according to at least one vector field template. A target location of the identified signature pattern is identified according to a corresponding electrode location.

U.S. Patent Application Publication 2004/0243012 describes a method and system for identifying and localizing a reentrant circuit isthmus in a heart of a subject during sinus rhythm is provided. The method may include (a) receiving electrogram signals from the heart during sinus rhythm via electrodes, (b) creating a map based on the electrogram signals, (c) determining, based on the map, a location of the reentrant circuit isthmus in the heart, and (d) displaying the location of the reentrant circuit isthmus.

U.S. Patent Application Publication 2017/0049348 describes a method for determining electrophysiology properties of tissue. The method comprising acquiring electrical signal data from a plurality of electrodes of one or more catheters, determining at least one electrode clique from the plurality of adjacent electrodes, computing local conduction velocity vectors for the at least one electrode clique, determining at least one catheter orientation independent indicator from which to classify an arrhythmia source based on one or more of an angular dependence parameter associated with a flow field of the local velocity conduction vectors, an eccentricity parameter reflecting the uniformity of local conduction velocity, and divergence and curl-like sums or closed path integral parameters associated with the local velocity vectors, and displaying a rhythm classification responsive to catheter movement thereby facilitating identification of types and causes of arrhythmia disorders.

SUMMARY OF THE INVENTION

An embodiment of the present invention provides a method including receiving (i) multiple electrophysiological (EP) signals acquired by multiple electrodes of a multi-electrode catheter that are in contact with tissue in a region of a cardiac chamber, and (ii) respective tissue locations at which the electrodes acquired the EP signals. First and second electrodes are selected among the multiple electrodes, the first electrodes positioned at first respective tissue locations of a first section of the region, and the second electrodes positioned at second respective tissue locations of a second section of the region. Based on the EP signals acquired by the selected electrodes, (i) local activation time (LAT) values for the first and second respective tissue locations, (ii) a first average LAT value for the first section, and (iii) a second average LAT value for the second section, are calculated and performing a comparison between the first and second average LAT values. A first representative location is determined within the first section, and a second representative location is determined within the second section. A propagation vector, which is indicative of a propagation of an EP wave that has generated the EP signals, is produced between the first and second representative locations, and based on the comparison between the first and second average LAT values. The propagation vector is presented to a user.

In some embodiments, the first and second electrodes include together a portion of the multiple electrodes, and the first and second sections: (i) include together a portion of the region, and (ii) have a common border dividing therebetween. In other embodiments, the method includes selecting, among the multiple electrodes: (i) third electrodes, different from the first and second electrodes, which are positioned at third respective tissue locations of a third section of the region, different from the first and second sections, and (ii) fourth electrodes, different from the first, second and third electrodes, which are positioned at fourth respective tissue locations of a fourth section of the region, different from the first, second and third sections; based on the EP signals acquired by the third and fourth electrodes, calculating (i) LAT values for the third and fourth respective tissue locations, (ii) a third average LAT value for the third section, and (iii) a fourth average LAT value for the fourth section, and compare between the third and fourth average LAT values; determining third and fourth representative location within the third and fourth sections, respectively; producing, between the third and fourth representative locations and based on the comparison between the third and fourth average LAT values, a given propagation vector indicative of a given propagation of a given EP wave that has generated the EP signals; and presenting the given propagation vector to the user.

In an embodiment, presenting the propagation vector and the given propagation vector includes overlaying, on a map of the cardiac chamber, one or both of: (i) a first arrow indicative of the propagation vector, and (ii) a second arrow indicative of the given propagation vector. In another embodiment, overlaying the first and second arrows includes using a graphical property of: (i) the first arrow to indicate a first speed of the EP wave between the first and second representative locations, and (ii) the second arrow to indicate a second speed of the given EP wave between the third and fourth representative locations.

There is additionally provided, in accordance with another embodiment of the present invention, a system including a processor and a display. The processor is configured to: (a) receive (i) multiple electrophysiological (EP) signals acquired by multiple electrodes of a multi-electrode catheter that are in contact with tissue in a region of a cardiac chamber, and (ii) respective tissue locations at which the electrodes acquired the EP signals, (b) select, among the multiple electrodes, first electrodes positioned at first respective tissue locations of a first section of the region, and second electrodes positioned at second respective tissue locations of a second section of the region, (c) based on the EP signals acquired by the selected electrodes, calculate: (i) local activation time (LAT) values for the first and second respective tissue locations, (ii) a first average LAT value for the first section, and (iii) a second average LAT value for the second section, and compare between the first and second average LAT values, (d) determine a first representative location within the first section, and a second representative location within the second section, and (e) produce, between the first and second representative locations, and based on the comparison between the first and second average LAT values, a propagation vector indicative of a propagation of an EP wave that has generated the EP signals. The display is configured to present the propagation vector to a user.

The present invention will be more fully understood from the following detailed description of the embodiments thereof, taken together with the drawings in which:

BRIEF DESCRIPTION OF THE DRAWINGS

FIG. 5 is a schematic distal view of electrodes of a catheter in contact with tissue, which are measuring EP signals and a presentation of one or more propagation vectors of one or more EP waves, in accordance with another embodiment of the present invention; and FIG. 6 is a flow chart that schematically illustrates a method for estimating and presenting one or more propagation vectors of one or more EP waves, in accordance with an embodiment of the present invention.

DETAILED DESCRIPTION OF EMBODIMENTS

Overview

Figure 1:
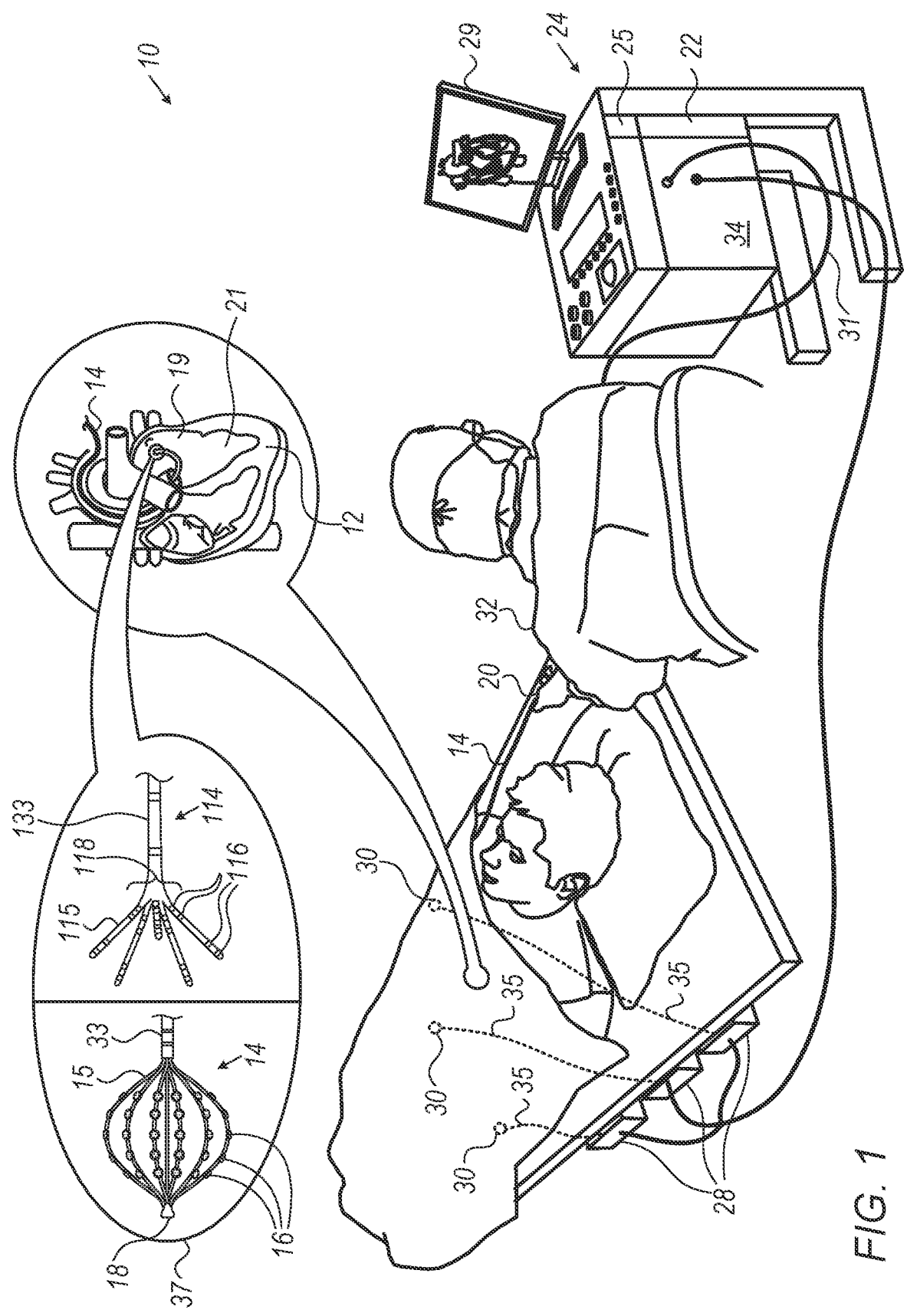
FIG. 1 is a schematic, pictorial illustration of an electrophysiological (EP) mapping system comprising different possible multi-electrode catheters, in accordance with embodiments of the present invention.

Intracardiac electrophysiological (EP) mapping is a catheter-based method that is sometimes applied to characterize cardiac EP wave propagation abnormalities, such those that cause an arrhythmia. In a typical catheter-based procedure, a distal end of a catheter, which comprises multiple sensing-electrodes, is inserted into the heart to sense a set of data points comprising measured locations over a wall tissue of a cardiac chamber and a respective set of EP signals, from which the EP mapping system can produce a map, such as an EP map, of the cardiac chamber.

For diagnostics in particular, the propagation direction of the EP wave at a region of the wall tissue may also be needed. The propagation direction of the cardiac wave can be found by creating a particular EP timing diagram map, called local activation time (LAT) map, of regions of the cardiac chamber.

However, determining a propagation vector of an EP wave in the cardiac chamber is a time-consuming process for any given region. Typically, LATs for a number of locations around the region need to be calculated, and then the vector derived from the LATs and the positions of the locations. Embodiments of the present invention that are described hereinafter provide efficient methods to acquire EP data and automatically calculate one or more propagation vector(s) in real time for a region in a cardiac chamber.

Among other features, the disclosed methods may use, in a particular way, various types of multi-electrode catheters, such as a basket catheter or a multi-arm catheter (e.g., PentaRay™ or OctaRay™, made by Biosense-Webster). The multi-electrode catheter is brought into contact with tissue (e.g., pressed against tissue) at an area comprising multiple regions of the cardiac chamber so that its "pole" (e.g., a distal tip where the spines of the basket connect, or from where the multiple arms originate) is on the chosen cardiac tissue regions, and electrodes on the spines/arms are in contact with wall tissue at tissue regions of the cardiac chamber to acquire EP signals.

In the context of the present disclosure and in the claims, the terms "arm," "spine," and "spline" are used interchangeably and refer to various configurations of branching elements of a catheter, which are configured to carry various types of electrodes for sensing EP signals and/or ablating heart tissue and/or sensing position signals indicative of the catheter position within the patient heart.

In some embodiments, a system for mapping EP waves comprises a processor and an output device, in the present example, a display. The processor is configured to receive multiple EP signals acquired by the electrodes of the multi-electrode catheter that are in contact with tissue in one region of a cardiac chamber. Note that the region typically comprises a portion of the area covered by the splines of the catheter described above. The processor is further configured to receive respective tissue locations at which the electrodes acquired the EP signals.

During the EP mapping procedure, a user of the system (e.g., a physician), may select one of more regions within the area of the heart chamber. In the following description, the method is applied to one selected region, however, the techniques described herein may be applied, mutatis mutandis, to different regions within the area covered by the catheter, so as to improve the mapping resolution of the EP wave(s) that propagate on the surface of the tissue in question.

In some embodiments, for each region selected by the physician, the processor is configured to select, among the multiple electrodes: (i) a set of first electrodes positioned at first respective tissue locations of a first section of the selected region, and (ii) a set of second electrodes positioned at second respective tissue locations of a second section of the selected region. Note that, because each region selected by the physician comprises a portion of the tissue in question, the first and second electrodes comprise together a portion of the aforementioned multiple electrodes of the catheter.

In some embodiments, based on the EP signals acquired by the selected electrodes, the processor is configured to calculate LAT values for the first and second respective tissue locations. The processor is further configured to calculate first and second average LAT values for the first and second sections, respectively, and to compare between the first and second average LAT values.

In some embodiments, the processor is configured to determine first and second representative locations within the first and second sections, respectively. For example, in the section with the lower average LAT value, the processor is configured to identify a location having the minimum LAT value. Similarly, in the section with the higher average LAT value, the processor is configured to identify a location with the maximum LAT value.

In some embodiments, based on the comparison between the first and second average LAT values, the processor is configured to produce, between the first and second representative locations of the selected region, a propagation vector. In the present example, the propagation vector is indicative of the propagation of the EP wave that has generated the EP signals that propagate on the surface of the heart tissue within the selected region.

In some embodiments, the display is configured to present the propagation vector, which was produced by the processor, to the physician or to any other user of the system.

In some embodiments, the processor is configured to draw an arrow, corresponding to the vector, on a map of the cardiac chamber. The length and/or the color of the arrow, are typically indicative of the direction and speed of the propagation of the EP wave.

In another embodiment, rather than calculate the velocity vector from the minimum of the LAT values at the section with the lower average LAT value to the maximum of the LAT values at the section with the higher average LAT value, the processor calculates a vector between a center-of-mass wall tissue location of the lower average LAT value and a center-of-mass wall tissue location of the higher average LAT value. To this end, the processor performs a center-of-mass calculation in the first section of a first wall tissue location of the lower average LAT value and a center-of-mass calculation in the second section of a second wall tissue location of the higher average LAT value. Subsequently, the processor calculates a center-of-mass propagation vector between the first and second center-of-mass locations of an EP wave that presumably generated the EP signals, and presents the center-of-mass propagation vector to a user. The center-of-mass calculations typically include calculating a weighted average of each center-of-mass location using two or more LAT values of each section as weights.

As described above, the processor is configured to apply the method to one or more different regions that are selected within the heart map by the physician. In some embodiments, for each selected region, the processor is configured to produce a separate propagation map. Moreover, the display is configured to display the propagation vectors overlaid on the respective selected regions of the heart map.

In some cases, within the area of interest (e.g., the area covered by the catheter electrodes), the physician may define a mapping resolution of the propagating EP waves, by selecting the regions of interest. In such cases, the processor is configured to provide the physician with the mapping of the one or more EP waves propagating within the area of interest, at the required resolution.

The disclosed techniques provide the physician with the ability to select (i) regions of interest, and (ii) the resolution-level, for mapping the propagation of EP waves on the surface of a selected area of the patient heart. Moreover, improved resolution of EP mapping may assist a physician with improving the quality of treating arrhythmias in the patient heart, or for treating any sort of electro-physiological disease in any other suitable patient organ.

System Description

FIG. 1 is a schematic, pictorial illustration of an electro-physiological (EP) mapping system 10 comprising different possible multi-electrode catheters, in accordance with embodiments of the present invention. System 10 may be configured to analyze substantially any physiological parameter or combinations of such parameters. In the description herein, by way of example, the analyzed signals are assumed to be intra-cardiac electrogram potential-time relationships. In order to fully characterize such relationships, the signals at various locations need to be referenced in time to each other, such as is done during LAT map generation. The time referencing is accomplished by measuring relative to a reference time (e.g., an instance in time), such as the beginning of each QRS complex of an ECG reference signal (i.e., the beginning of every heartbeat). The method for generating an LAT map is described in U.S. Pat. No. 9,050,011, cited above.

As noted above, system 10 comprises a multi-electrode catheter, which can be, among numerous possible options, a basket catheter 14 or a multi-arm catheter 114 (e.g., a PentaRay™ catheter), both of which are shown in inset 37. The description hereinafter collectively calls the above catheter options, "catheter 14/114," which means the embodiments described hereinafter hold for either of these multi-electrode catheter types.

Multi-electrode catheter 14/114 is inserted by a physician 32 through the patient's vascular system into a chamber or vascular structure of a heart 12. Physician 32 brings the catheter's distal tip 18/118 into contact with (e.g., presses the tip distally against) wall tissue 19 of a cardiac chamber 21, at an EP mapping target tissue site. The catheter typically comprises a handle 20 which has suitable controls to enable physician 32 to steer, position and orient the distal end of the catheter as desired for EP mapping.

The multi-electrode catheter 14/114 is coupled to a console 24, which enables physician 32 to observe and regulate the functions of the catheter. To aid physician 32, the distal portion of the catheter may contain various sensors, such as contact force sensors (not shown) and a magnetic sensor 33/133 that provides position, direction, and orientation signals to a processor 22, located in a console 24. Processor 22 may fulfill several processing functions as described below. In particular, electrical signals can be conveyed to and from heart 12 from electrodes 16/116 located at or near the distal tip 18 of catheter 14/114 via cable 34 to console 24. Pacing signals and other control signals may be conveyed from console 24 through cable 34 and electrodes 16/116 to heart 12.

Console 24 includes an output device, such as but not limited to a display 29, which is configured to display items produced by processor 22, as will be described in detail below. Signal processing circuits in an electrical interface 34 typically receive, amplify, filter, and digitize signals from catheter 14/114, including signals generated by the above-noted sensors and the plurality of sensing electrodes 16. The digitized signals are received and used by console 24 and the positioning system to compute the position and orientation of catheter 14/114 and to analyze the EP signals from electrodes 16/116 as described in further detail below.

During the disclosed procedure, the respective locations of electrodes 16/116 are tracked. The tracking may be performed, for example, using the CARTO® 3 system, produced by Biosense-Webster. Such a system measures impedances between electrodes 16/116 and a plurality of external electrodes 30 that are coupled to the body of the patient. For example, three external electrodes 30 may be coupled to the patient's chest, and another three external electrodes may be coupled to the patient's back. (For ease of illustration, only chest electrodes are shown in FIG. 1.). Wire connections 35 link the console 24 with body surface electrodes 30 and other components of a positioning subsystem to measure location and orientation coordinates of catheter 14/114. The method of tracking electrode 16 positions based on electrical signals, named Active Current Location (ACL), is implemented in various medical applications, as, for example, the aforementioned CARTO®3 system. Details of an ACL subsystem and process are provided in U.S. Pat. No. 8,456,182, which is assigned to the assignee of the present patent application and whose disclosure is incorporated herein by reference.

In some embodiments, system 10 comprises, in addition to, or instead of, the ACL tracking subsystem, a magnetic position tracking subsystem that determines the position and orientation of magnetic sensor 33, at a distal end of catheter 14/114, by generating magnetic fields in a predefined working volume, and sensing these fields at the catheter using field generating coils 28. As electrodes 16/116 have known locations on arms 15/115, and known relationships to one another, once catheter 14/114 is tracked magnetically in the heart, the location of each of electrodes 16/116 in the heart becomes known. A suitable magnetic position tracking subsystem is described in U.S. Pat. Nos. 7,756,576 and 7,536,218, which are assigned to the assignee of the present patent application and whose disclosure is incorporated herein by reference.

Based on the EP signals from electrodes 16/116 having tracked locations, electrical activation maps may be prepared, according to the methods disclosed in U.S. Pat. Nos. 6,226,542, and 6,301,496, and 6,892,091, which are assigned to the assignee of the present patent application and whose disclosure is incorporated herein by reference.

Processor 22 uses software stored in a memory 25 to operate system 10. The software may be downloaded to processor 22 in electronic form, over a network, for example, or it may, alternatively or additionally, be provided and/or stored on non-transitory tangible media, such as magnetic, optical, or electronic memory. In particular, processor 22 runs a dedicated algorithm as disclosed herein, including in FIG. 4, that enables processor 22 to perform the disclosed steps, as further described below.

The example illustration shown in FIG. 1 is chosen purely for the sake of conceptual clarity. Other types of EP sensing geometries, such as of a balloon catheter comprising electrode segments, described in U.S. patent application Ser. No. 16/708,285, titled, "Catheter with Plurality of Sensing Electrodes Used as Ablation Electrodes," filed Dec. 9, 2019, whose disclosure is incorporated herein by reference, may also be employed.

System 20 typically comprises additional modules and elements that are not directly related to the disclosed techniques, and thus are intentionally omitted from FIG. 1 and from the corresponding description. The elements of system 20 and the methods described herein may be further applied, for example, to control an ablation of tissue of heart 12.

Figure 2B:
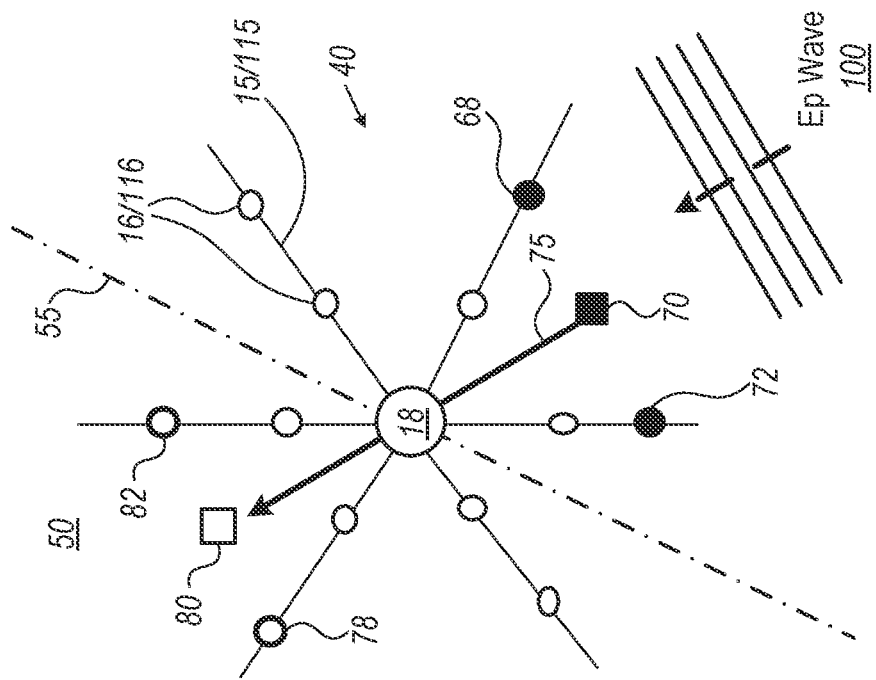
FIGS. 2A and 2B are schematic distal views of electrodes of one of the catheters of FIG. 1 in contact with tissue and measuring electrophysiological (EP) signals, in accordance with embodiments of the present invention.
Figure 2A:
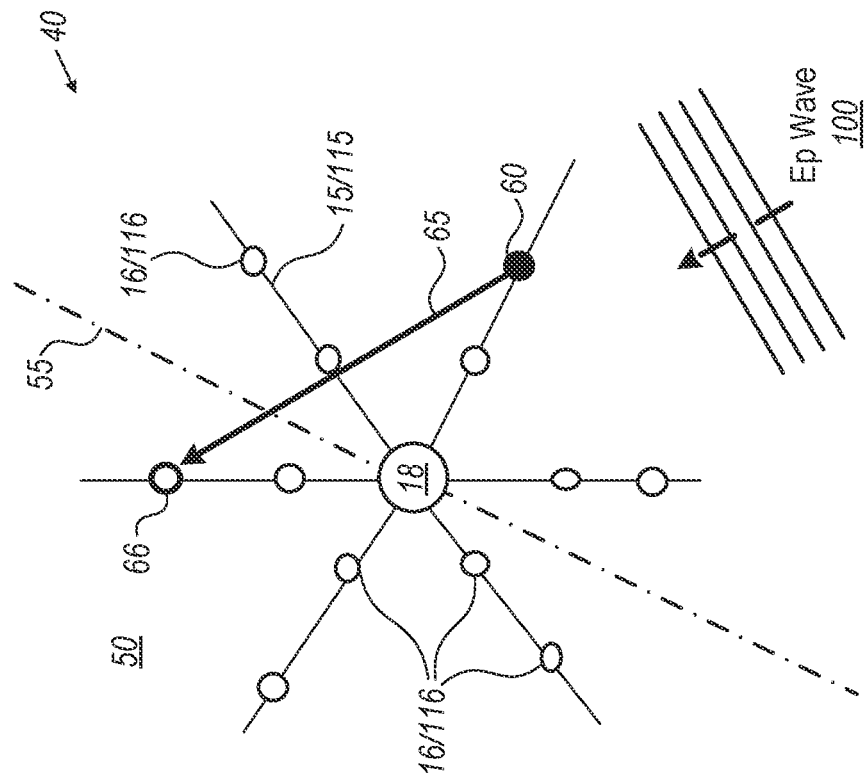

Analyzing Multi-Electrode Catheter Signals to Determine EP Wave Propagation Vector FIGS. 2A and 2B are schematic distal views of electrodes 16/116 of one of the catheters of FIG. 1 in contact with tissue and measuring electrophysiological (EP) signals, in accordance with embodiments of the present invention. The figures further show tissue 50 and a distal portion 40 of the spines or arms 15/115 of catheter 14/114 that are pressed against tissue 50, as viewed at a distal direction from a location proximally to the spines or arms on the axis of the catheter. The spines or arms 15/115 are coupled together at distal tip 18/118 of the catheter.

In some embodiments, processor 22 divides the splines/arms into two sections, using a virtual plane 55 containing the axis of the catheter. Processor 22 may select the sections, i.e., select plane 55, arbitrarily or in accordance with a certain selection criterion. Then, using EP signals acquired from each electrode 16/116, the processor calculates the LAT values at the electrode locations in each section. Processor 22 then finds which of the two sections is characterized by lower average LAT values (e.g., has the lower average LAT value out of the two sections), and which is characterized by higher average LAT values (e.g., has the higher average value out of the two sections).

In the embodiment shown in FIG. 2A, for the section with the lower average LAT value, the processor finds the minimum LAT value, and its location 60. For the section with the higher average LAT value, the processor finds the maximum LAT value, and its location 66. Locations 60 and 66 are referred to herein as "representative locations" because each of them represents its entire respective section by a single data point.

From the known displacements (distance and direction) between the two representative locations, and the known times (the difference in LAT values), the processor calculates a velocity vector (speed and direction) of an EP wave 100 that generated the signals as it propagates in tissue under the catheter. The processor may then draw an arrow 65, corresponding to the vector, on a map of the cardiac chamber. The length of arrow 65, and/or its color, may be set to correspond to the speed.

In the embodiment shown in FIG. 2B, rather than calculating the velocity vector from the minimum of the LAT values at the section with the lower average LAT value to the maximum of the LAT values at the section with the higher average LAT value, the vector is calculated between the centers-of-mass locations of the lower average and higher average LAT values, using the following equation to find the center of mass locations:

$$\bar{r} = \frac{\sum_i LAT_i r_i}{\sum_i LAT_i} \qquad \text{Eq. 1}$$

In FIG. 2B, by way of example, i=1, 2 for each center of mass location. That is, center-of-mass wall tissue location 70 is calculated from Eq. 1 using LAT values and respective locations 68 and 72, and center-of-mass wall tissue location 80 is calculated using LAT values and respective locations 78 and 82. The processor may then draw an arrow 75 corresponding to the vector between locations 70 and 80. Thus, in the example of FIG. 2B, the centers-of-mass of the two sections (locations 70 and 80) serve as the representative locations. In alternative embodiments, processor 22 may choose the representative locations in the two sections in any other suitable way.

The illustrations in FIGS. 2A and 2B are conceptual and brought by way of example. Actual catheter structure may vary. For example, the number of spines or arms may be larger than shown.

Figure 3:
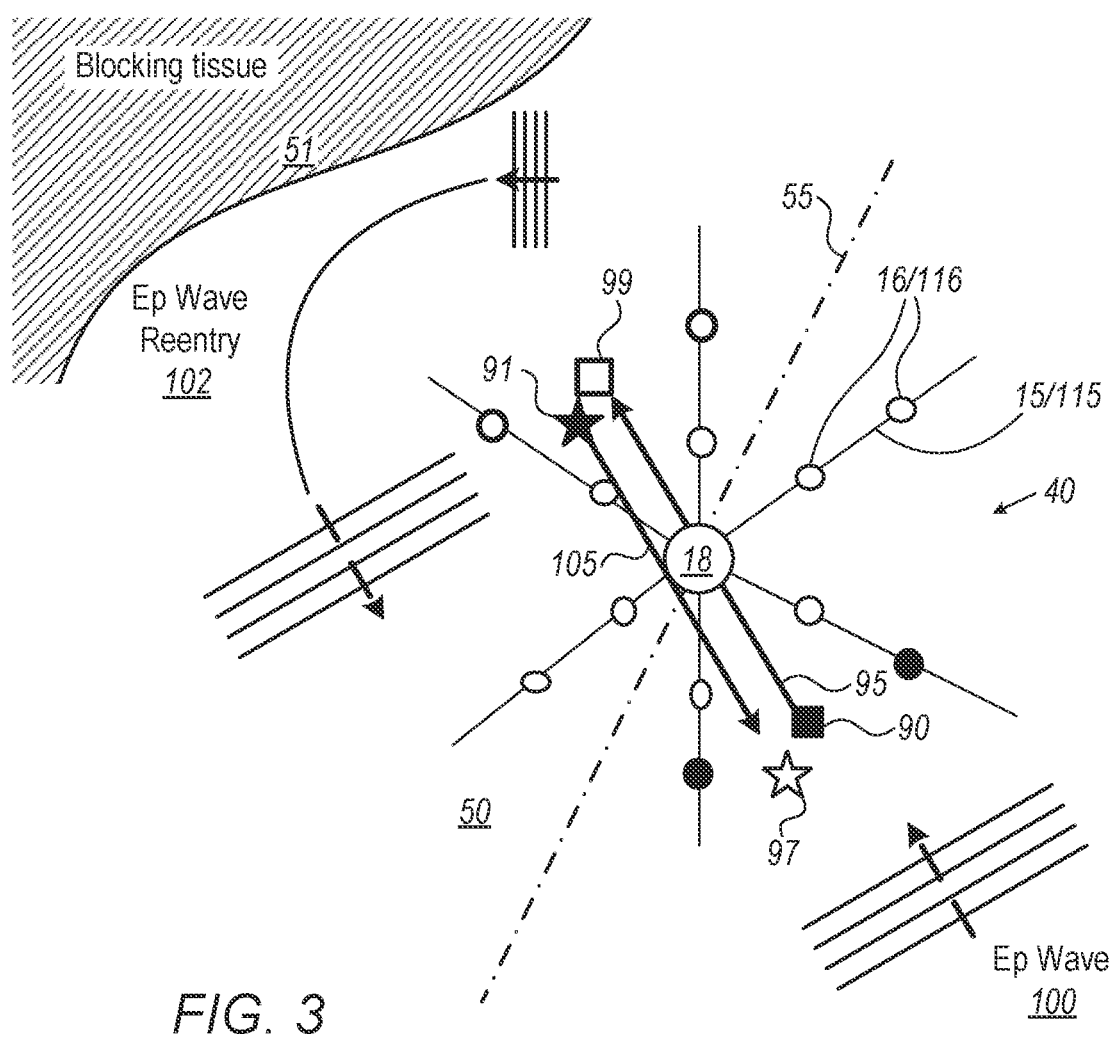
FIG. 3 is a schematic distal view of electrodes of one of the catheters of FIG. 1 in contact with tissue and measuring electrophysiological (EP) signals, in accordance with another embodiment of the present invention.

FIG. 3 is a schematic distal view of electrodes 16/116 of one of the catheters of FIG. 1 in contact with tissue and measuring electrophysiological (EP) signals, in accordance with another embodiment of the present invention. The catheter 14/114 layout is the same as in FIGS. 2A and 2B, but with the catheter placed at a different tissue location where EP wave reentry occurs.

As noted above, in case of a reentry type of arrhythmia, the velocity vector at the region may oscillate in direction (backwards and forwards). This occurs typically if the catheter is at a junction where EP wave 100 is actually alternating in direction, for example, due to the wave encountering an aberrant unidirectional propagation blocking tissue 52. In this case, the two EP wave vectors (one of incident EP wave 100 and the other of reentry EP wave 102) may be displayed on the screen as two respective arrows, 95 and 97, each with a different brightness/thickness/length/color according to their relative magnitudes. In FIG. 3 the vectors are calculated using the center-of-mass calculation method of FIG. 2B. One respective vector points from center-of-mass location 90 to center-of-mass location 99, and the other from center-of-mass location 91 to center-of-mass location 97.

Figure 4:
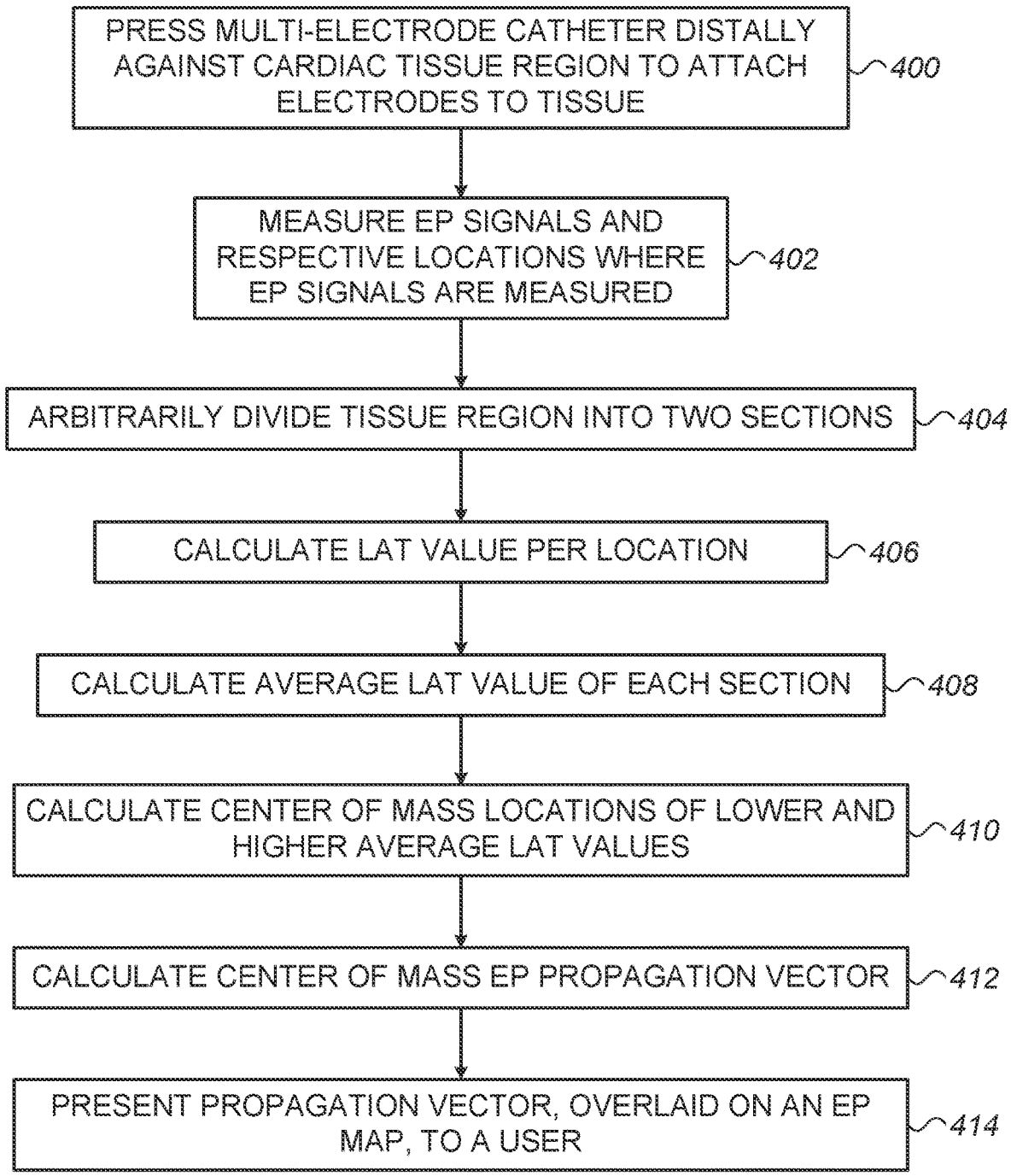
FIG. 4 is a flow chart that schematically illustrates a method and algorithm for estimating and presenting a propagation vector of an electrophysiological (EP) wave, in accordance with an embodiment of the present invention.

FIG. 4 is a flow chart that schematically illustrates a method and algorithm for estimating and presenting a propagation vector of an electrophysiological (EP) wave 100, in accordance with an embodiment of the present invention. The algorithm, according to the presented embodiment, carries out a process that begins with physician 32 pressing catheter 14/114 against cardiac tissue region to bring part of electrodes 16/116 to contact with tissue, at a catheter placement step 400.

Then, system 10 measures electrode locations over wall tissue 19 of cardiac chamber 21 and a respective set of EP signals at the locations, generated by an EP wave 100, at a measurement step 402.

Next, processor 22 arbitrarily divides the region into two sections, at a region division step 404.

Next, processor 22 calculates an LAT value at each electrode location, at an LAT calculation step 406.

Next, at average LAT calculation step 408, processor 22 calculates the average LAT value per each section. Typically, one section has a lower average LAT value than the other.

Next, at average LAT location calculation step 410, processor 22 calculates center-of-mass locations of the lower and higher average LAT values, using the method described in FIG. 2B.

Using the center-of-mass locations, processor 22 calculates the center-of-mass EP wave propagation vector of EP wave 100, at a vector calculation step 414.

Finally, at a propagation-vector presentation step 410, processor 22 overlays (e.g., draws) an arrow, corresponding to the vector, on a map of the cardiac chamber. The length of the arrow, and/or its color, may be set to correspond to the speed.

The example flow chart shown in FIG. 4 is chosen purely for the sake of conceptual clarity. The present embodiment also comprises additional steps of the algorithm, such as operating other sensors mounted on the catheter, such as contact force sensors, which have been omitted from the disclosure herein purposely on order to provide a more simplified flow chart.

FIG. 5 is a schematic distal view of a distal-end assembly (DEA) 500 having multiple electrodes 505 in contact with tissue of heart 12, and a presentation of propagation vectors 508 and 518 of one or more EP waves, in accordance with another embodiment of the present invention. DEA 500 may replace, for example, basket catheter 14 or multi-arm catheter 114 of FIG. 1 above.

In some embodiments, DEA 500 may have a basket shape or a multi-arm shape and comprises multiple splines 502 that may replace, for example, arms 15 or arms 115 of FIG. 1 above. Each spline 502 comprises one or more electrodes 505 (described in detail below), which may replace, for example, electrodes 16 or electrodes 116 of FIGS. 2A, 2B and 3 above.

In some embodiments, processor 22 receives EP signals acquired by electrodes 505 of DEA 500 and respective locations in the tissue of heart 12 (also referred to herein as tissue locations) at which electrodes 505 acquired the EP signals. In the present example, the respective locations are received from magnetic sensor 33 or 133 described in FIG. 1 above In some embodiments, physician 32 may select within the tissue of heart 12 one or more regions of interest. In the present example, physician 32 may select regions 510 and 520 shown by respective perimeters, which may be displayed over DEA 500.

In some embodiments, processor 22 is configured to select, among electrodes 505 or DEA 500, electrodes 505a positioned at first respective tissue locations of a first section 510a of region 510, and electrodes 505b positioned at second respective tissue locations of a second section 510b of region 510. Note that region 510 covers only a portion of the tissue in question, and has a border 504 defining sections 510a and 510b. In other words, sections 510a and 510b have a common border (e.g., border 504) dividing therebetween.

In some embodiments, based on the EP signals acquired by electrodes 505a and 505b, processor 22 is configured to calculate: (i) LAT values for the first and second respective tissue locations, (ii) a first average LAT value for section 510a, and (iii) a second average LAT value for section 510b. Processor 22 is further configured to compare between the first and second average LAT values.

In some embodiments, processor 22 is configured to determine a first representative location, referred to herein as a location 506a, within the first section, and a second representative location within the second section, referred to herein as a location 506b. The determination of locations 506a and 506b may be carried out using any suitable calculation and/or criterion. For example, a center-of-mass of the respective section, or a combination of the positions and calculated LAT values of the electrodes within the respective section, or the calculation performed by eq. 1 described above, or any other suitable calculation and/or criterion.

In some embodiments, based on the comparison between the first and second average LAT values, processor 22 is configured to produce, between locations 506a and 506b, propagation vector 508, which is indicative of the propagation of the EP wave (e.g., EP wave 100 described in FIGS. 2A and 2B above) that has generated the aforementioned EP signals. In the present example, in the section with the lower average LAT value, processor 22 is configured to identify a location having the minimum LAT value. Similarly, in the section with the higher average LAT value, processor 22 is configured to identify a location with the maximum LAT value. As described above, processor 22 may present an arrow, which corresponds to propagation vector 508, on the map of the cardiac chamber.

In some embodiments, the length and/or a color of the arrow may be indicative of the propagation velocity of EP wave 100 within section 510, and the direction of the arrow may be indicative of the propagation direction of EP wave within section 510.

In some embodiments, processor 22 is configured to display to physician 32, on display 29 or on any other suitable output device, propagation vector 508 over the map of at least a portion (e.g., a chamber) of heart 12.

Reference is now made to region 520 of FIG. 5. In some embodiments, physician 32 may select one or more regions in addition to region 510. The other regions may have the same area to that of region 510 or a different area, such as in the case of region 520, which is larger than region 520 and has a different number of electrodes, as will be described herein. In the present example, the area covered by region 520 is also a portion of the tissue of question, which is covered by DEA 500.

In some embodiments, using the same technique described in region 510 above, processor 22 is configured to: (a) select, among electrodes 505, (i) electrodes 505c of a spline 502c, which are positioned at third respective tissue locations of a section 520a of region 520, and (ii) electrodes 505d of a spline 502d, which are positioned at fourth respective tissue locations of a section 520b of region 520. Note that one or more of electrodes 505c and 505d are different from electrodes 505a and 505b, and at least part of sections 520a and 520b is different from sections 510a and 510b. Moreover, each section from among sections 510a, 510b, 520a and 520b, may have any suitable number of electrodes from any suitable number of splines. The number of electrodes are defined for each region and/or section based on a selection of physician 32, and may or may not be adjusted, e.g., based on a recommendation from processor 22.

In some embodiments, processor 22 is configured to calculate, based on the EP signals acquired by electrodes 505c and 505d, (i) LAT values for the third and fourth respective tissue locations, (ii) a third average LAT value for section 520a, and (iii) a fourth average LAT value for section 520b, and compare between the third and fourth average LAT values.

In some embodiments, processor 22 is configured to determine third and fourth representative location, also referred to herein as locations 516a and 516b, respectively, within sections 520a and 520b, respectively.

In some embodiments, based on the comparison between the third and fourth average LAT values, processor 22 is configured to produce, between locations 516a and 516b, propagation vector 518, also referred to herein as a given propagation vector. In the present example, propagation vector 518 is indicative of the propagation of a given EP wave (e.g., EP wave 100 or another EP wave propagating in region 520 over the surface of heart 12) that has generated the EP signals acquired by electrodes 505c and 505d.

In some embodiments, display 29 is configured to present both propagation vectors 508 and 518 to physician 32 or to any other user of system 10. Note that the embodiments described in FIG. 5 may use at least some of the techniques described for example in FIGS. 2A, 2B and 3. However, by producing (within the tissue area covered by DEA 500) multiple regions, such as regions 510 and 520 (each of which covering a portion of the tissue in question), processor 22 is configured to provide physician 32 with multiple wave propagation vectors (e.g., vectors 508 and 518) of the one or more EP waves propagating over the surface of heart 12. In other words, for each tissue area covered by CEA 500, processor 22 is configured to provide physician 32 with higher granularity (i.e., resolution) of the wave propagation vectors compared to that described in FIGS. 2A, 2B and 3 above.

This particular configuration of DEA 500 and the analysis of EP waves are shown by way of example, in order to illustrate certain problems that are addressed by embodiments of the present invention and to demonstrate the application of these embodiments in enhancing the performance of such an EP mapping system. Embodiments of the present invention, however, are by no means limited to this specific sort of example distal-end assembly and/or selected regions, sections and electrodes, and the principles described herein may similarly be applied to other sorts of EP mapping procedures and systems for EP mapping in any suitable medical application.

FIG. 6 is a flow chart that schematically illustrates a method for estimating and presenting one or more propagation vectors of one or more EP waves, in accordance with an embodiment of the present invention.

The method begins at an EP signals receiving step 600 with processor 22 receiving measurements of EP signals, and respective locations. In the present example, the EP signals are received from the electrodes of CEA 500 placed in contact with the aforementioned cardiac tissue, as described in FIG. 5 above, and the respective locations are determined based on signals received from magnetic sensor 33 or 133 described in FIG. 1 above.

At an electrode selection step 602, based on one or more regions selected by physician 32, processor 22 selects among the electrodes of DEA 500 within each region, two groups of electrodes located in two different sections of the selected region. Note that each of the selected regions comprises a portion of the area covered by DEA 500. For example, in region 510, processor 22 selects electrodes 505a and 505b of sections 510a and 510b, respectively, as described in detail in FIG. 5 above.

At a calculation and comparison step 604, based on the EP signals, processor 22 calculates (i) LAT values for the positions of electrodes 505a and 505b, and (ii) first and second average LAT values obtained for sections 510a and 510b, respectively. Moreover, processor 22 compares between the first and second average LAT values. The techniques for calculating the LAT values and average LAT values are described in FIGS. 1-5 above.

At a representative location determination step 606, processor 22 determines first and second representative locations within the first and second selected sections, respectively. In the present example, processor 22 determines locations 506a and 506b within sections 510a and 510b, respectively. The techniques for determining the representative locations are described in detail in FIGS. 1-5 above.

At a propagation vector presentation step 608 that concludes the method, processor 22 produces between locations 506a and 506b, propagation vector 508, which is indicative of the propagation of the EP wave (e.g., EP wave 100) that generates the EP signals. Moreover, processor 22 presents propagation vector 508 to physician 32, e.g., on display 29. In some embodiments, processor presents propagation vector 508 over an anatomical or electro-anatomical (EA) map of at least a portion of heart 12.

In some embodiments, physician 32 may select one or more additional regions, such as region 520 shown in FIG. 5 above, and processor 22 may apply the techniques described in steps 602-608 to region 520. Moreover, processor 22 may present, e.g., over the EA map on display 29, both propagation vectors 508 and 518, so as to provide physician 32 with high-resolution mapping of the propagation of the EP wave on the surface of heart 12.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
receiving: (i) multiple electrophysiological (EP) signals acquired by multiple electrodes disposed on a distal end assembly of a multi-electrode catheter having multiple splines or arms, the electrodes configured to be in contact with tissue in a region of a cardiac chamber, and (ii) respective tissue locations at which the electrodes acquired the EP signals;
selecting, among the multiple electrodes, two or more first electrodes disposed on a first spline or arm and positioned at first respective tissue locations of a first section of the region, and two or more second electrodes disposed on a first spline or arm and positioned at second respective tissue locations of a second section of the region;
based on the EP signals acquired by the selected electrodes, calculating: (i) local activation time (LAT) values for the first and second respective tissue locations, (ii) a first average LAT value for the first section, and (iii) a second average LAT value for the second section, and comparing between the first and second average LAT values;
determining a first representative location within the first section, and a second representative location within the second section;
producing, between the first and second representative locations and based on the comparison between the first and second average LAT values, a propagation vector indicative of a propagation of an EP wave that has generated the EP signals; and
displaying the propagation vector to a user.

2. The method according to claim 1, wherein the first and second electrodes comprise together a portion of the multiple electrodes, and wherein the first and second sections: (i) comprise together a portion of the region, and (ii) have a common border dividing therebetween.

3. The method according to claim 1, and comprising selecting, among the multiple electrodes: (i) third electrodes, different from the first and second electrodes, which are configured to be positioned at third respective tissue locations of a third section of the region, different from the first and second sections, and (ii) fourth electrodes, different from the first, second and third electrodes, which are configured to be positioned at fourth respective tissue locations of a fourth section of the region, different from the first, second and third sections; based on the EP signals acquired by the third and fourth electrodes, calculating (i) LAT values for the third and fourth respective tissue locations, (ii) a third average LAT value for the third section, and (iii) a fourth average LAT value for the fourth section, and compare between the third and fourth average LAT values; determining third and fourth representative location within the third and fourth sections, respectively; producing, between the third and fourth representative locations and based on the comparison between the third and fourth average LAT values, a given propagation vector indicative of a given propagation of a given EP wave that has generated the EP signals; and displaying the given propagation vector to the user.

4. The method according to claim 3, wherein displaying the propagation vector and the given propagation vector comprises overlaying, on a map of the cardiac chamber, one or both of: (i) a first arrow indicative of the propagation vector, and (ii) a second arrow indicative of the given propagation vector.

5. The method according to claim 4, wherein overlaying the first and second arrows comprises using a graphical property of: (i) the first arrow to indicate a first speed of the EP wave between the first and second representative locations, and (ii) the second arrow to indicate a second speed of the given EP wave between the third and fourth representative locations.

6. A system, comprising:
a processor, which is configured to:
receive: (i) multiple electrophysiological (EP) signals acquired by multiple electrodes disposed on a distal end assembly of a multi-electrode catheter having multiple splines or arms, the electrodes configured to be in contact with tissue in a region of a cardiac chamber, and (ii) respective tissue locations at which the electrodes acquired the EP signals;

select, among the multiple electrodes, two or more first electrodes disposed on a first spline or arm and positioned at first respective tissue locations of a first section of the region, and two or more second electrodes disposed on a second spline or arm and positioned at second respective tissue locations of a second section of the region;

based on the EP signals acquired by the selected electrodes, calculate: (i) local activation time (LAT) values for the first and second respective tissue locations, (ii) a first average LAT value for the first section, and (iii) a second average LAT value for the second section, and compare between the first and second average LAT values;

determine a first representative location within the first section, and a second representative location within the second section; and produce, between the first and second representative locations, and based on the comparison between the first and second average LAT values, a propagation vector indicative of a propagation of an EP wave that has generated the EP signals; and a display, which is configured to present the propagation vector to a user.

7. The system according to claim 6, wherein the first and second electrodes comprise together a portion of the multiple electrodes, and wherein the first and second sections: (i) comprise together a portion of the region, and (ii) have a common border dividing therebetween.

8. The system according to claim 6, wherein the processor is configured to: (a) select, among the multiple electrodes, (i) third electrodes, different from the first and second electrodes, which are configured to be positioned at third respective tissue locations of a third section of the region, different from the first and second sections, and (ii) fourth electrodes, different from the first, second and third electrodes, which are configured to be positioned at fourth respective tissue locations of a fourth section of the region, different from the first, second and third sections; (b) calculate, based on the EP signals acquired by the third and fourth electrodes: (i) LAT values for the third and fourth respective tissue locations, (ii) a third average LAT value for the third section, and (iii) a fourth average LAT value for the fourth section, and compare between the third and fourth average LAT values; (c) determine third and fourth representative location within the third and fourth sections, respectively; and (d) produce, between the third and fourth representative locations and based on the comparison between the third and fourth average LAT values, a given propagation vector indicative of a given propagation of a given EP wave that has generated the EP signals, and wherein the display is configured to present the given propagation vector to the user.

9. The system according to claim 8, wherein the processor is configured to overlay, on a map of the cardiac chamber, one or both of: (i) a first arrow indicative of the propagation vector, and (ii) a second arrow indicative of the given propagation vector.

10. The system according to claim 9, wherein the processor is configured to use a graphical property of: (i) the first arrow to indicate a first speed of the EP wave between the first and second representative locations, and (ii) the second arrow to indicate a second speed of the given EP wave between the third and fourth representative locations.

11. The system according to claim 8, wherein the third electrodes comprise two or more third electrodes disposed on a third spline or arm and the fourth electrodes comprise two or more fourth electrodes disposed on a fourth spline or arm.

\* \* \* \* \*